(12) United States Patent
Hostetler et al.

(10) Patent No.: US 7,452,898 B2
(45) Date of Patent: *Nov. 18, 2008

(54) PHOSPHONATE COMPOUNDS

(75) Inventors: Karl Y. Hostetler, Del Mar, CA (US); James R. Beadle, San Diego, CA (US); Ganesh D. Kini, Bristow, VA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/506,292

(22) Filed: Aug. 17, 2006

(65) Prior Publication Data

US 2006/0281706 A1 Dec. 14, 2006

Related U.S. Application Data

(63) Continuation of application No. 11/100,882, filed on Apr. 6, 2005, now Pat. No. 7,094,772, which is a continuation of application No. 10/759,345, filed on Jan. 15, 2004, now Pat. No. 7,034,014, which is a continuation of application No. 10/148,374, filed as application No. PCT/US00/33079 on Dec. 4, 2000, now Pat. No. 6,716,825.

(60) Provisional application No. 60/205,719, filed on May 19, 2000, provisional application No. 60/168,813, filed on Dec. 3, 1999.

(51) Int. Cl.
*A61K 31/505* (2006.01)

(52) U.S. Cl. .................................................... 514/274

(58) Field of Classification Search ................ 514/274; 544/243
See application file for complete search history.

(56) References Cited

U.S. PATENT DOCUMENTS

| 1,944,530 | A | 1/1934 | Schonburg | 558/92 |
|---|---|---|---|---|
| 5,223,263 | A | 6/1993 | Hostetler et al. | 424/450 |
| 5,376,649 | A | 12/1994 | Pohjala et al. | 514/108 |
| 5,411,947 | A * | 5/1995 | Hostetler et al. | 514/43 |
| 5,463,092 | A | 10/1995 | Hostetler et al. | 554/40 |
| 5,627,185 | A | 5/1997 | Gosselin et al. | 514/81 |
| 5,672,697 | A | 9/1997 | Buhr et al. | 536/26.7 |
| 5,922,695 | A | 7/1999 | Arimilli et al. | 514/81 |
| 5,977,089 | A | 11/1999 | Arimilli et al. | 514/81 |
| 6,716,825 | B2 | 4/2004 | Hostetler et al. | 514/52 |
| 7,034,014 | B2 | 4/2006 | Hostetler et al. | |
| 7,094,772 | B2 | 8/2006 | Hostetler et al. | |
| 7,098,197 | B2 | 8/2006 | Hostetler et al. | |

FOREIGN PATENT DOCUMENTS

| EP | 0632048 | 1/1995 |
|---|---|---|
| EP | 0897709 | 2/1999 |
| GB | 1280788 | 7/1972 |
| WO | WO 96/40088 | 6/1996 |
| WO | WO 99/08685 | 2/1999 |
| WO | WO 00/04032 | 1/2000 |

OTHER PUBLICATIONS

Niemi et al., "Bisphosphonate Prodrugs: Synthesis and in Vitro Evaluation of Novel Acyloxyalkyl Esters of Clodronic Acid," *J. Med. Chem.*, vol. 42, pp. 5053-5058 (1999).

Serafinowska et al., "Synthesis and in Vivo Evaluation of Prodrugs of (-[2-Phosphonomethoxy)ethoxy]adenine" *J. Med. Chem.*, vol. 38, No. 8, pp. 1372-1379, 1995.

Wan, W.B., et al., "Comparison of the antiviral activities of alkoxyalkyl and alkyl esters of cidofovir against human and murine cytomegalovirus replication in vitro," *Antimicrob. Agents Chemother.*, 49(2):656-662 (Feb. 2005).

Jones et al., "Minireview: Nucleotide Prodrugs," *Antiviral Research*, 27:1-17, 1995.

Notari, Robert E., "Prodrug Design," *Pharmac. Ther.*, 14:25-53, 1981.

* cited by examiner

*Primary Examiner*—Taofiq A Solola
(74) *Attorney, Agent, or Firm*—DLA Piper LLP (US)

(57) ABSTRACT

The present invention relates to phosphonate compounds, compositions containing them, processes for obtaining them, and their use for treating a variety of medical disorders, e.g., osteoporosis and other disorders of bone metabolism, cancer, viral infections, and the like.

11 Claims, 2 Drawing Sheets

PHOSPHONATE COMPOUNDS

CROSS REFERENCE TO RELATED APPLICATIONS

This application is a continuation application of U.S. application Ser. No. 11/100,882 filed Apr. 6, 2005, now issued as U.S. Pat. No. 7,094,772; which is a continuation application of U.S. application Ser. No. 10/759,345 filed Jan. 15, 2004, now issued as U.S. Pat. No. 7,034,014; which is a continuation application of U.S. application Ser. No. 10/148,374 filed Nov. 6, 2002, now issued as U.S. Pat. No. 6,716,825; which is a 35 USC § 371 National Stage application of PCT Application No. US00/33079 filed Dec. 4, 2000; which claims the benefit under 35 USC § 119(e) to U.S. Application Ser. No. 60/205,719 filed May 19, 2000, now abandoned and to U.S. Application Ser. No. 60/168,813 filed Dec. 3, 1999, now abandoned. The disclosure of each of the prior applications is considered part of and is incorporated by reference in the disclosure of this application.

GRANT INFORMATION

This invention was made with government support under Grant No. GM24979 awarded by the National Institutes of Health. The United States government has certain rights in this invention.

BACKGROUND OF THE INVENTION

1. Field of the Invention

The present invention relates to novel phosphonate compounds, compositions containing them, processes for producing them, and their use for treating a variety of medical disorders, e.g., osteoporosis and other disorders of bone metabolism, cancer, viral infections, and the like.

2. Background Information

Phosphonate compounds have long been known to provide a variety of therapeutic benefits. A particular class of therapeutically beneficial phosphonate compounds are the bisphosphonates, i.e., pyrophosphate analogs wherein the central oxygen atom of the pyrophosphate bond is replaced by carbon. Various substituent groups may be attached to this central carbon atom to produce derivative bisphosphonate compounds having various degrees of pharmacological potency. These derivatives have the general structure:

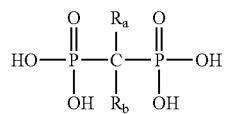

wherein $R_a$ and $R_b$ may independently be selected from hydroxyl, amino, sulfhydryl, halogen, or a variety of alkyl or aryl groups, or a combination of such groups, which may be further substituted. Examples include Etidronate, wherein $R_a$ is $CH_3$ and $R_b$ is OH; Clodronate, dichloromethylene bisphosphonic acid ($Cl_2MDP$), wherein $R_a$ and $R_b$ are Cl, Pamidronate, 3-amino-1-hydroxypropylidene bisphosphonic acid, wherein $R_a$ is ethylamino and $R_b$ is hydroxyl; Alendronate, 4-amino-1-hydroxybutylidene bisphosphonic acid, wherein $R_a$ is propylamino and $R_b$ is hydroxyl; Olpadronate, 3-dimethylamino-1-hydroxypropylidene bisphosphonic acid, wherein $R_a$ is dimethylaminoethyl and $R_b$ is hydroxyl; and amino-olpadronate (IG-9402), 3-(N,N-dimethylamino)-1-aminopropylidene bisphosphonate, wherein $R_a$ is N,N-dimethylaminoethyl and $R_b$ is $NH_2$.

Bisphosphonates and their substituted derivatives have the intrinsic property of inhibiting bone resorption in vivo. Bisphosphonates also act by inhibiting apoptosis (programmed cell death) in bone-forming cells. Indications for their use therefore include the treatment and prevention of osteoporosis, treatment of Paget's disease, metastatic bone cancers, hyperparathyroidism, rheumatoid arthritis, algodistrophy, sterno-costo-clavicular hyperostosis, Gaucher's disease, Engleman's disease, and certain non-skeletal disorders. (Papapoulos, S. E., in *Osteoporosis*, R. Marcus, D. Feldman and J. Kelsey, eds., Academic Press, San Diego, 1996. p. 1210, Table 1).

Although bisphosphonates have therapeutically beneficial properties, they suffer from pharmacological disadvantages as orally administered agents. One drawback is low oral availability: as little as 0.7% to 5% of an orally administered dose is absorbed from the gastrointestinal tract. Oral absorption is further reduced when taken with food. Further, it is known that some currently available bisphosphonates, e.g., FOSAMAX™ (Merck; alendronate sodium), SKELID™ (Sanofi, tiludronate) and ACTONE™ (Procter and Gamble, risedronate) have local toxicity, causing esophageal irritation and ulceration. Other bisphosphonates, like amino-olpadronate, lack anti-resorptive effects (Van Beek, E. et al., J. Bone Miner Res 11(10):1492-1497 (1996) but inhibit osteocyte apoptosis and are able to stimulate net bone formation (Plotkin, L. et al., J Clin Invest 104(10): 1363-1374 (1999) and U.S. Pat. No. 5,885,973). It would therefore, be useful to develop chemically modified bisphosphonate derivatives that maintain or enhance the pharmacological activity of the parent compounds while eliminating or reducing their undesirable side effects.

In addition to bisphosphonates, monophosphonates are also known to provide therapeutic benefits. One class of therapeutically beneficial monophosphonates are the antiviral nucleotide phosphonates, such as, for example, cidofovir, cyclic cidofovir, adefovir, tenofovir, and the like, as well as the 5'-phosphonates and methylene phosphonates of azidothymidine, ganciclovir, acyclovir, and the like. In compounds of this type, the 5'-hydroxyl of the sugar moiety, or its equivalent in acyclic nucleosides (ganciclovir, penciclovir, acyclovir) which do not contain a complete sugar moiety, is replaced with a phosphorus-carbon bond. In the case of the methylene phosphonates, a methylene group replaces the 5'-hydroxyl or its equivalent, and its carbon atom is, in turn, covalently linked to the phosphonate. Various AZT structures are presented below, including compounds contemplated for use in the practice of the present invention. AZT itself is shown on the left. Compound A is AZT-monophosphate which has the usual phosphodiester link between the sugar and the phosphate. In contrast, in compounds B (AZT 5'-phosphonate) and C (AZT 5'-methylene phosphonate), the 5'-hydroxyl of 3'-azido, 2',3'-dideoxyribose is absent and has been replaced by either a phosphorus-carbon bond (AZT phosphonate) or by a methylene linked by a phosphorus-carbon bond (AZT methylene phosphonate). Compounds B and C are examples of compounds useful in the practice of the present invention.

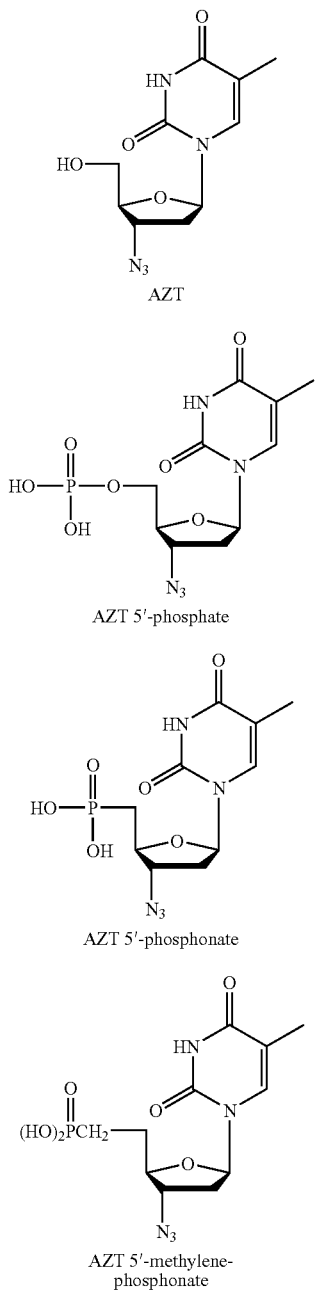

AZT

AZT 5'-phosphate

AZT 5'-phosphonate

AZT 5'-methylene-phosphonate

Compounds of this type may be active as antiproliferative or antiviral nucleotides. Upon cellular metabolism, two additional phosphorylations occur to form the nucleotide phosphonate diphosphate which represents the equivalent of nucleoside triphosphates. Antiviral nucleotide phosphonate diphosphates are selective inhibitors of viral RNA or DNA polymerases or reverse transcriptases. That is to say, their inhibitory action on viral polymerases is much greater than their degree of inhibition of mammalian cell DNA polymerases $\alpha$, $\beta$ and $\gamma$ or mammalian RNA polymerases. Conversely, the antiproliferative nucleotide phosphonate diphosphates inhibit cancer cell DNA and RNA polymerases and may show much lower selectivity versus normal cellular DNA and RNA polymerases. Since nucleotide phosphonates are poorly absorbed from the GI tract they frequently require parenteral administration (e.g. cidofovir). Furthermore, the negatively charged phosphonate moiety may interfere with cellular penetration, resulting in reduced activity as antivirals or antiproliferatives. Invention compounds may surprisingly overcome the disadvantages of this class of agents.

Pharmacologically active agents of antiviral phosphonates are known; the following U.S. Patents describe other approaches for nucleotide phosphonate analogs: U.S. Pat. No. 5,672,697 (Nuleoside-5'-methylene phosphonates), U.S. Pat. No. 5,922,695 (Antiviral phosphonomethoxy nucleotide analogs), U.S. Pat. No. 5,977,089 (Antiviral phosphonomethoxy nucleotide analogs), U.S. Pat. No. 6,043,230 (Antiviral phosphonomethoxy nucleotide analogs), U.S. Pat. No. 6,069,249. The preparation and use of alkylglycerol phosphates covalently linked to non-phosphonate containing drugs having amino, carboxyl, hydroxyl or sulfhydryl functional groups have previously been disclosed. These prodrugs optionally comprise a linker group or one or two additional phosphates esters between the drug and the alkyl glycerol phosphate (U.S. Pat. No. 5,411,947 and U.S. patent application Ser. No. 08/487,081). Partial esters of chloromethane-diphosphonic acid are known (U.S. Pat. No. 5,376,649) and dianhydrides of clodronate have been reported (Ahlmark, et al., J Med Chem 42: 1473-1476 (1999)). However, the partial esters were found to not release the active bisphosphonate by chemical or biochemical conversion (Niemi, R. et al, J Chrom B 701:97-102 (1997)). Prodrugs comprising alkylglycerol phosphate residues attached to antiviral nucleosides (U.S. Pat. No. 5,223,263) or phosphono-carboxylates (U.S. Pat. No. 5,463,092) have also been described.

There is, therefore, a continuing need for less toxic, more effective pharmaceutical agents to treat a variety of disorders, such as those caused by viral infection and inappropriate cell proliferation, e.g., cancer. Thus, it is an object of the present invention to develop chemically modified phosphonate derivatives of pharmacologically active agents, e.g., antiviral and anti-neoplastic pharmaceutical agents. These modified derivatives increase the potency of the parent compound while minimizing deleterious side effects when administered to a subject in need thereof.

BRIEF DESCRIPTION OF THE INVENTION

The invention provides analogs of phosphonate compounds. Phosphonate compounds contemplated for use in accordance with the invention include those that decrease bone resorption or inhibit osteoblast or osteocyte apoptosis, as well as those that improve the bioactivity, selectivity, or bioavailability of nucleotide phosphonate analogs which are useful for the treatment of cancer, various viral infections, and the like. Invention compounds comprise phosphonates covalently linked (directly or indirectly through a linker molecule) to a substituted or unsubstituted alkylglycerol, alkylpropanediol, alkylethanediol, or related moiety. In another aspect of the present invention, there are provided pharmaceutical formulations containing the analogs of phosphonate compounds described herein.

In accordance with another aspect of the present invention, there are provided a variety of therapeutic methods, e.g., methods for treating or preventing bone resorption in a mammal, methods for increasing bone formation by preventing osteoblast and osteocyte apoptosis, methods for increasing bone mass and strength, methods for treating viral infections, methods for treating disorders caused by inappropriate cell proliferation, e.g., cancer, and the like.

DETAILED DESCRIPTION OF THE INVENTION

Figure 1:
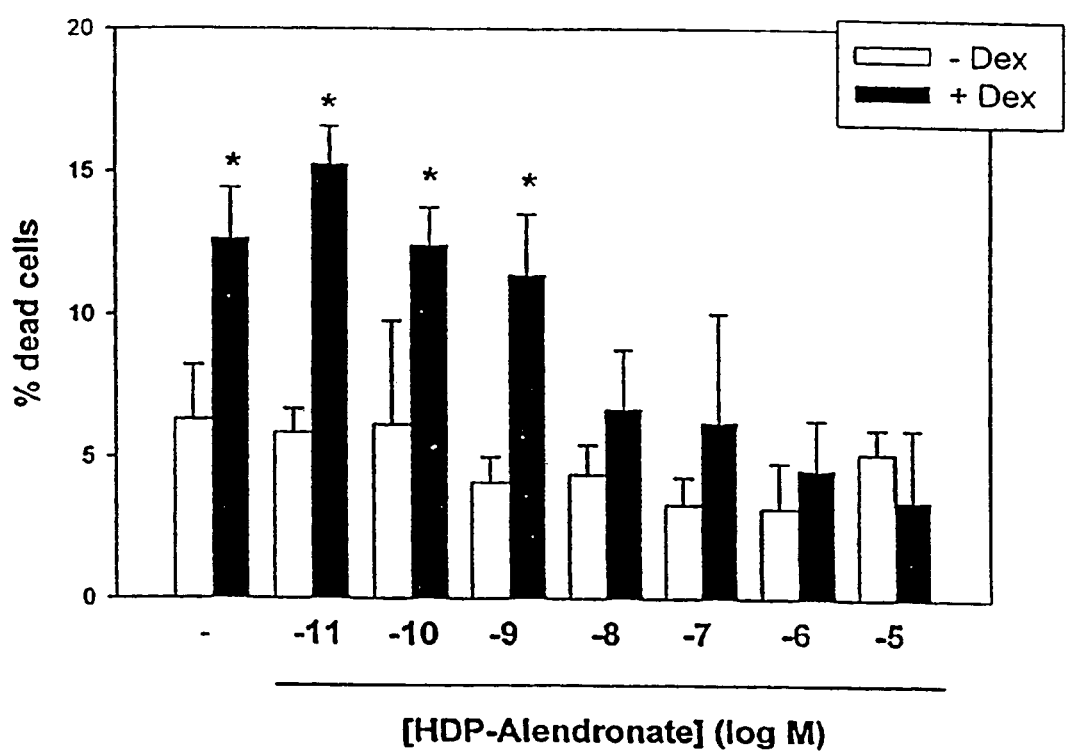
FIG. 1 summarizes the effect of a compound according to the invention, 1-O-hexadecyloxypropane alendronate, on dexamethasone-induced apoptosis of MLO-Y4 osteocytic cells. Bars represent the mean±SD of 3 independent measurements. Open bars represent the absence of dexamethasone and darkened bars represent the presence of $10^{-4}$ M dexamethasone.

The phosphonate compounds of the invention have the structure:

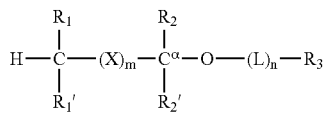

wherein:

$R_1$ and $R_1'$ are independently —H, optionally substituted —O($C_1$-$C_{24}$)alkyl, —O($C_1$-$C_{24}$)alkenyl, —O($C_1$-$C_{24}$)acyl, —S($C_1$-$C_{24}$)alkyl, —S($C_1$-$C_{24}$)alkenyl, or —S($C_1$-$C_{24}$)acyl, wherein at least one of $R_1$ and $R_1'$ are not —H, and wherein said alkenyl or acyl moieties optionally have 1 to 6 double bonds, $R_2$ and $R_2'$ are independently —H, optionally substituted —O($C_1$-$C_7$)alkyl, —O($C_1$-$C_7$)alkenyl, —S($C_1$-$C_7$)alkyl, —S($C_1$-$C_7$)alkenyl, —O($C_1$-$C_7$)acyl, —S($C_1$-$C_7$)acyl, —N($C_1$-$C_7$)acyl, —NH($C_1$-$C_7$)alkyl, —N(($C_1$-$C_7$)alkyl)$_2$, oxo, halogen, —NH$_2$, —OH, or —SH;

$R_3$ is a pharmaceutically active phosphonate, bisphosphonate or a phosphonate derivative of a pharmacologically active compound, linked to a functional group on optional linker L or to an available oxygen atom on Cα

X, when present, is:

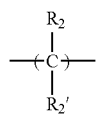

L is a valence bond or a bifunctional linking molecule of the formula -J-(CR$_2$)$_t$-G-, wherein t is an integer from 1 to 24, J and G are independently —O—, —S—, —C(O)O—, or —NH—, and R is —H, substituted or unsubstituted alkyl, or alkenyl;

m is an integer from 0 to 6; and n is 0 or 1.

In preferred embodiments, m=0, 1 or 2. In these preferred embodiments, $R_2$ and $R_2'$ are preferably H, and the prodrugs are then ethanediol, propanediol or butanediol derivatives of a therapeutic phosphonate. A preferred ethanediol phosphonate species has the structure

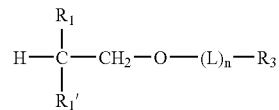

wherein $R_1$, $R_1'$, $R_3$, L, and n are as defined above.

A preferred propanediol species has the structure:

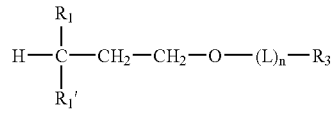

wherein m=1 and $R_1$, $R_1'$, $R_3$, L and n are as defined above in the general formula.

A preferred glycerol species has the structure:

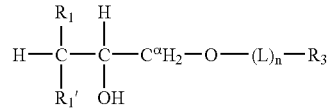

wherein m=1, $R_2$=H, $R_2'$=OH, and $R_2$ and $R_2'$ on $C^\alpha$ are both —H. Glycerol is an optically active molecule. Using the stereospecific numbering convention for glycerol, the sn-3 position is the position which is phosphorylated by glycerol kinase. In compounds of the invention having a glycerol residue, the -(L)$_n$-$R_3$ moiety may be joined at either the sn-3 or sn-1 position of glycerol.

In all species of the pharmacologically active agents of the invention, $R_1$ is preferably an alkoxy group having the formula —O—(CH$_2$)t-CH$_3$, wherein t is 0-24. More preferably t is 11-19. Most preferably t is 15 or 17.

Preferred $R_3$ groups include bisphosphonates that are known to be clinically useful, for example, the compounds:

Etidronate: 1-hydroxyethylidene bisphosphonic acid (EDHP);

Clodronate: dichloromethylene bisphosphonic acid (Cl2MDP);

Tiludronate: chloro-4-phenylthiomethylene bisphosphonic acid;

Pamidronate: 3-amino-1-hydroxypropylidene bisphosphonic acid (ADP);

Alendronate: 4-amino-1-hydroxybutylidene bisphosphonic acid;

Olpadronate: 3-dimethylamino-1-hydroxypropylidene bisphosphonic acid (dimethyl-APD);

Ibandronate: 3-methylpentylamino-1-hydroxypropylidene bisphosphonic acid (BM 21.0955);

EB-1053: 3-(1-pyrrolidinyl)-1-hydroxypropylidene bisphosphonic acid;

Risedronate: 2-(3-pyridinyl)-1-hydroxy-ethylidene bisphosphonic acid;

Amino-Olpadronate: 3-(N,N-diimethylamino-1-aminopropylidene) bisphosphonate (IG9402), and the like.

$R_3$ may also be selected from a variety of phosphonate-containing nucleotides (or nucleosides which can be derivatized to their corresponding phosphonates), which are also contemplated for use herein. Preferred nucleosides include those useful for treating disorders caused by inappropriate cell proliferation such as 2-chloro-deoxyadenosine, 1-β-D-arabinofuranosyl-cytidine (cytarabine, ara-C), fluorouridine, fluorodeoxyuridine (floxuridine), gemcitabine, cladribine, fludarabine, pentostatin (2'-deoxycoformycin), 6-mercaptopurine, 6-thioguanine, and substituted or unsubstituted 1-β-D-arabinofuranosyl-guanine (ara-G), 1-β-D-arabinofuranosyl-adenosine (ara-A), 1-β-D-arabinofuranosyl-uridine (ara-U), and the like.

Nucleosides useful for treating viral infections may also be converted to their corresponding 5'-phosphonates for use as an $R_3$ group. Such phosphonate analogs typically contain either a phosphonate (—$PO_3H_2$) or a methylene phosphonate (—$CH_2$—$PO_3H_2$) group substituted for the 5'-hydroxyl of an antiviral nucleoside. Some examples of antiviral phosphonates derived by substituting —PO3H2 for the 5'-hydroxyl are:

3'-azido-3',5'-dideoxythymidine-5'-phosphonic acid (AZT phosphonate)

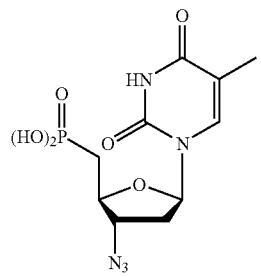

Hakimelahi, G. H.; Moosavi-Movahedi, A. A.; Sadeghi, M. M.; Tsay, S-C.; Hwu, J. R., J. Med. Chem. 1995, 38:4648-4659.

3',5'-dideoxyhymidine-2'-ene-5'-phosphonic acid (d4T phosphonate)

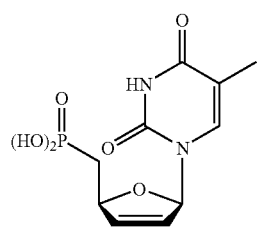

Hakimelahi, G. H.; Moosavi-Movahedi, A. A.; Sadeghi, M. M.; Tsay, S-C.; Hwu, J. R., J. Med. Chem. 1995, 38:4648-4659.

2',3',5'-trideoxycytidine-5'-phosphonic acid (ddC phosphonate)

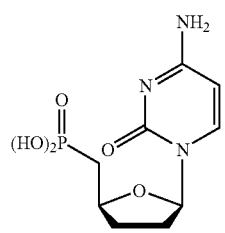

Kofoed, T.; Ismail, A. E. A. A.; Pedersen, E. B.; Nielsen, C., Bull. Soc. Chim. Fr. 1997, 134:59-65.

9-[3-(phosphonomethoxy)propyl]adenine (Adefovir)

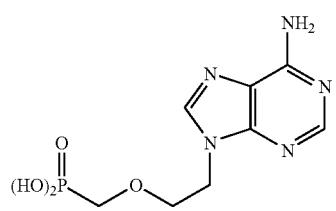

Kim, C. U.; Luh, B. Y.; Misco, P. F.; Bronson, J. J.; Hitchcock, M. J. M.; Ghazzouli, I.; Martin, J. C., J. Med. Chem. 1990, 33:1207-1213.

Some examples of antiviral phosphonates derived by substituting —CH$_2$—PO$_3$H$_2$ for the 5'-hydroxyl are:

| | | |
|---|---|---|
| Ganciclovir phosphonate | 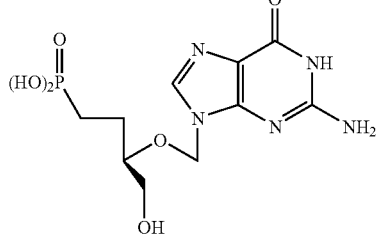 | Huffman, J. H.; Sidwell, R. W.; Morrison, A. G.; Coombs, J.; Reist, E. J., Nucleoside Nucleotides, 1994, 13:607-613. |
| Acyclovir phosphonate | 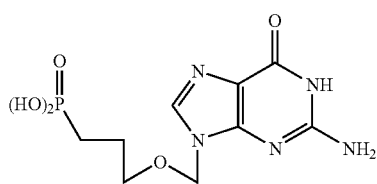 | Huffman, J. H.; Sidwell, R. W.; Morrison, A. G.; Coombs, J.; Reist, E. J., Nucleoside Nucleotides, 1994, 13:607-613. |
| Ganciclovir cyclic phosphonate | 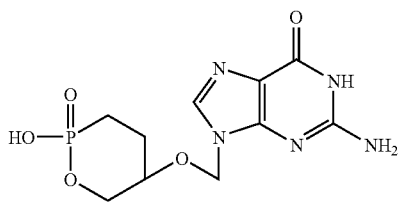 | Smee, D. F.; Reist, E. J., Antimicrob. Agents Chemother. 1996, 40:1964-1966. |
| 3'-thia-2',3'-dideoxycytidine-5'-phosphonic acid | 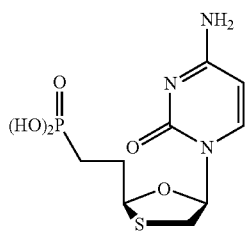 | Kraus, J. L.; Nucleosides Nucleotides, 1993, 12:157-162. |

Other preferred antiviral nucleotide phosphonates contemplated for use in the practice of the invention are derived similarly from antiviral nucleosides including ddA, ddI, ddG, L-FMAU, DXG, DAPD, L-dA, L-dI, L-(d)T, L-dC, L-dG, FTC, penciclovir, and the like.

Additionally, antiviral phosphonates such as cidofovir, cyclic cidofovir, adefovir, tenofovir, and the like, may be used as an R$_3$ group in accordance with the present invention.

Certain compounds of the invention possess one or more chiral centers, e.g. in the sugar moieties, and may thus exist in optically active forms. Likewise, when the compounds contain an alkenyl group or an unsaturated alkyl or acyl moiety there exists the possibility of cis- and trans-isomeric forms of the compounds. Additional asymmetric carbon atoms can be present in a substituent group such as an alkyl group. The R—and S-isomers and mixtures thereof, including racemic mixtures as well as mixtures of cis- and trans-isomers are contemplated by this invention. All such isomers as well as mixtures thereof are intended to be included in the invention. If a particular stereoisomer is desired, it can be prepared by methods well known in the art by using stereospecific reactions with starting materials that contain the asymmetric centers and are already resolved or, alternatively, by methods that lead to mixtures of the stereoisomers and resolution by known methods.

Many phosphonate compounds exist that can be derivatized according to the invention to improve their pharmacologic activity, or to increase their oral absorption, such as, for example, the compounds disclosed in the following patents, each of which are hereby incorporated by reference in their entirety: U.S. Pat. No. 3,468,935 (Etidronate), U.S. Pat. No. 4,327,039 (Pamidronate), U.S. Pat. No. 4,705,651 (Alendronate), U.S. Pat. No. 4,870,063 (Bisphosphonic acid derivatives), U.S. Pat. No. 4,927,814 (Diphosphonates), U.S. Pat. No. 5,043,437 (Phosphonates of azidodideoxynucleosides), U.S. Pat. No. 5,047,533 (Acyclic purine phosphonate nucleotide analogs), U.S. Pat. No. 5,142,051 (N-Phosphonylmethoxyalkyl derivatives of pyrimidine and purine bases), U.S. Pat. No. 5,183,815 (Bone acting agents), U.S. Pat. No. 5,196,409 (Bisphosphonates), U.S. Pat. No. 5,247,085 (Antiviral purine compounds), U.S. Pat. No. 5,300,671 (Gem-diphosphonic acids), U.S. Pat. No. 5,300,687 (Trifluoromethylbenzylphosphonates), U.S. Pat. No. 5,312,954 (Bis- and tetrakis-phosphonates), U.S. Pat. No. 5,395,826

(Guanidinealkyl-1,1-bisphosphonic acid derivatives), U.S. Pat. No. 5,428,181 (Bisphosponate derivatives), U.S. Pat. No. 5,442,101 (Methylenebisphosphonic acid derivatives), U.S. Pat. No. 5,532,226 (Trifluoromethybenzylphosphonates), U.S. Pat. No. 5,656,745 (Nucleotide analogs), U.S. Pat. No. 5,672,697 (Nuleoside-5'-methylene phosphonates), U.S. Pat. No. 5,717,095 (Nucleotide analogs), U.S. Pat. No. 5,760,013 (Thymidylate analogs), U.S. Pat. No. 5,798,340 (Nucleotide analogs), U.S. Pat. No. 5,840,716 (Phosphonate nucleotide compounds), U.S. Pat. No. 5,856,314 (Thio-substituted, nitrogen-containing, heterocyclic phosphonate compounds), U.S. Pat. No. 5,885,973 (olpadronate), U.S. Pat. No. 5,886,179 (Nucleotide analogs), U.S. Pat. No. 5,877,166 (Enantiomericaily pure 2-aminopurine phosphonate nucleotide analogs), U.S. Pat. No. 5,922,695 (Antiviral phosphonomethoxy nucleotide analogs), U.S. Pat. No. 5,922,696 (Ethylenic and allenic phosphonate derivatives of purines), U.S. Pat. No. 5,977,089 (Antiviral phosphonomethoxy nucleotide analogs), U.S. Pat. No. 6,043,230 (Antiviral phosphonomethoxy nucleotide analogs), U.S. Pat. No. 6,069,249 (Antiviral phosphonomethoxy nucleotide analogs); Belgium Patent No. 672205 (Clodronate); European Patent No. 753523 (Amino-substituted bisphosphonic acids); European Patent Application 186405 (geminal diphosphonates); and the like.

Certain bisphosphonate compounds have the ability to inhibit squalene synthase and to reduce serum cholesterol levels in mammals, including man. Examples of these bisphosphonates are disclosed, for example, in U.S. Pat. Nos. 5,441,946 and 5,563,128 to Pauls et al. Phosphonate derivatives of lipophilic amines, both of which are hereby incorporated by reference in their entirety. Analogs of these squalene synthase inhibiting compounds according to the invention, and their use in the treatment of lipid disorders in humans are within the scope of the present invention. Bisphosphonates of the invention may be used orally or topically to prevent or treat periodontal disease as disclosed in U.S. Pat. No. 5,270,365, hereby incorporated by reference in its entirety.

As used herein, the term "alkyl" refers to a monovalent straight or branched chain or cyclic radical of from one to twenty-four carbon atoms, including methyl, ethyl, n-propyl, isopropyl, n-butyl, isobutyl, tert-butyl, n-hexyl, and the like.

As used herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As used herein, "alkenyl" refers to straight or branched chain hydrocarbyl groups having one or more carbon-carbon double bonds, and having in the range of about 2 up to 24 carbon atoms, and "substituted alkenyl" refers to alkenyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, the term "bond" or "valence bond" refers to a linkage between atoms consisting of an electron pair.

As used herein, the term "pharmaceutically acceptable salts" refers to both acid and base addition salts.

As used herein, the term "prodrug" refers to derivatives of pharmaceutically active compounds that have chemically or metabolically cleavable groups and become the pharmaceutically active compound by solvolysis or under in vivo physiological conditions.

Phosphonate analogs, comprising therapeutically effective phosphonates (or phosphonate derivatives of therapeutically effective compounds) covalently linked by a hydroxyl group to a 1-O-alkyglycerol, 3-O-alkylglycerol, 1-S-alkylthioglycerol, or alkoxy-alkanol, may be absorbed more efficiently in the gastrointestinal tract than are the parent compounds. An orally administered dose of the analog is taken up intact from the gastrointestinal tract of a mammal and the active drug is released in vivo by the action of endogenous enzymes. Phosphonate analogs of the invention may also have a higher degree of bioactivity than the corresponding underivatized compounds.

The compounds of the present invention are an improvement over alkylglycerol phosphate prodrugs described in the prior art because the phosphonate-containing moiety is linked directly to the alkyl-glycerol or the alkoxy-alkanol moiety and because the presence of the phosphonate bond prevents enzymatic conversion to the free drug. Other linkers between these groups can be present in the improved analogs. For example, bifunctional linkers having the formula —O—$(CH_2)_n$—C(O)O—, wherein n is 1 to 24, can connect the phosphonate to the hydroxyl group of the alkoxy-alkanol or alkylglycerol moiety.

The foregoing allows the phosphonate of the invention to achieve a higher degree of oral absorption. Furthermore, cellular enzymes, but not plasma or digestive tract enzymes, will convert the conjugate to a free phosphonate. A further advantage of the alkoxy-alkanol phosphonates is that the tendency of co-administered food to reduce or abolish phosphonate absorption is greatly reduced or eliminated, resulting in higher plasma levels and better compliance by patients.

Compounds of the invention can be administered orally in the form of tablets, capsules, solutions, emulsions or suspensions, inhaled liquid or solid particles, microencapsulated particles, as a spray, through the skin by an appliance such as a transdermal patch, or rectally, for example, in the form of suppositories. The lipophilic prodrug derivatives of the invention are particularly well suited for transdermal absorption administration and delivery systems and may also be used in toothpaste. Administration can also take place parenterally in the form of injectable solutions.

The compositions may be prepared in conventional forms, for example, capsules, tablets, aerosols, solutions, suspensions, or together with carriers for topical applications. Pharmaceutical formulations containing compounds of this invention can be prepared by conventional techniques, e.g., as described in *Remington's Pharmaceutical Sciences*, 1985.

The pharmaceutical carrier or diluent employed may be a conventional solid or liquid carrier. Examples of solid carriers are lactose, sucrose, talc, gelatin, agar, pectin, acacia, magnesium stearate, stearic acid, or lower alkyl ethers of cellulose. Examples of liquid carriers are syrup, peanut oil, olive oil, phospholipids, fatty acids, fatty acid amines, polyoxyethylene or water. The carrier or diluent may include any sustained release material known in the art, such as glyceryl monostearate or distearate, alone or mixed with a wax.

If a solid carrier is used for oral administration, the preparation may be tabletted or placed in a hard gelatin capsule in powder or pellet form. The amount of solid carrier will vary widely, but will usually be from about 25 mg to about 1 gm. If a liquid carrier is used, the preparation may be in the form of a syrup, emulsion, soft gelatin capsule, or sterile injectable liquid such as an aqueous or non-aqueous liquid suspension or solution.

Tablets are prepared by mixing the active ingredient (that is, one or more compounds of the invention), with pharmaceutically inert, inorganic or organic carrier, diluents, and/or excipients. Examples of such excipients which can be used for tablets are lactose, maize starch or derivatives thereof, talc, stearic acid or salts thereof. Examples of suitable excipients for gelatin capsules are vegetable oils, waxes, fats, semisolid, and liquid polyols. The bisphosphonate prodrugs can also be made in microencapsulated form.

For nasal administration, the preparation may contain a compound of the invention dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

Pharmaceutical compositions of this invention for parenteral injection comprise pharmaceutically acceptable sterile aqueous or non-aqueous liquids, dispersions, suspensions or emulsions as well as sterile powders for reconstitution into sterile injectable solutions or dispersions just prior to use.

Suitable excipients for the preparation of solutions and syrups are water, polyols, sucrose, invert sugar, glucose, and the like. Suitable excipients for the preparation of injectable solutions are water, alcohols, polyols, glycerol, vegetable oils, and the like.

The pharmaceutical products can additionally contain any of a variety of added components, such as, for example, preservatives, solubilizers, stabilizers, wetting agents, emulsifiers, sweeteners, colorants, flavorings, buffers, coating agents, antioxidants, diluents, and the like.

Optionally, the pharmaceutical compositions of the invention may comprise a compound according to the general formula combined with one or more compounds exhibiting a different activity, for example, an antibiotic or other pharmacologically active material. Such combinations are within the scope of the invention.

This invention provides methods of treating mammalian disorders related to bone metabolism, viral infections, inappropriate cell proliferation, and the like. The methods particularly comprise administering to a human or other mammal in need thereof a therapeutically effective amount of the prodrugs of this invention. Indications appropriate to such treatment include senile, post-menopausal or steroid-induced osteoporosis, Paget's disease, metastatic bone cancers, hyperparathyroidism, rheumatoid arthritis, algodystrophy, stemo-costoclavicular hyperostosis, Gaucher's disease, Engleman's disease, certain non-skeletal disorders and periodontal disease, human immunodeficiency virus (HIV), influenza, herpes simplex virus (HSV), human herpes virus 6, cytomegalovirus (CMV), hepatitis B virus, Epstein-Barr virus (EBV), varicella zoster virus, lymphomas, hematological disorders such as leukemia, and the like.

In accordance with one aspect of the invention, there are provided methods of preventing or treating bone loss in mammals, especially humans, which method comprises" administering to the human or mammal a therapeutically effective amount of the compounds of this invention. The bone resorption inhibiting bisphosphonate prodrugs of the invention are useful therapeutically to oppose osteoclast-mediated bone resorption or bone loss in conditions wherein the bisphosphonate from which the prodrug is prepared has been found efficacious. Indications appropriate to such treatment include osteoporosis, particularly in postmenopausal women, the osteoporosis that accompanies long-term glucocortcoid therapy, and Paget's disease of bone. The bisphosphonate compound clodronate (Ostac, Boehringer-Mannheim, Mannheim, Germany) has also been found to reduce osseous as well as visceral metastases in breast cancer patients at high risk for distant metastases (Diel, I. J. et al. (1998) New Engl. J. Med. 339(60 357-363). Efficacy of the bisphosphonate prodrugs of the invention can be evaluated according to the same methods as for the parent compound. These comprise comparative measurement of bone mineral density of the lumber spine, femoral neck, trochanter, forearm and total body, together with measurements of vertebral fractures, spinal deformities and height in osteoporosis, bone scans or radiographic identification of bone lesions in metastatic disease, and the like.

In accordance with another aspect of the invention, there are provided methods for increasing bone mass and strength in mammals, especially humans, by administering bone anabolism-promoting compounds of the invention which inhibit osteoblast and osteocyte apoptosis, leading to greater net rates of bone formation, while not substantially altering osteoclast functions (Plotkin et al., J Clin Invest 104:1363-1374 (1999) and Van Beek et al., J Bone Min Res 11:1492 (1996)).

In accordance with yet another aspect of the invention, there are provided methods for treating disorders caused by viral infections. Indications appropriate to such treatment include susceptible viruses such as human immunodeficiency virus (HIV), influenza, herpes simplex virus (HSV), human herpes virus 6, cytomegalovirus (CMV), hepatitis B and C virus, Epstein-Barr virus (EBV), varicella zoster virus, and diseases caused by *orthopox* viruses (e.g., *variola major* and minor, vaccinia, smallpox, cowpox, camelpox, monkeypox, and the like), ebola virus, papilloma virus, and the like.

In accordance with still another aspect of the invention, there are provided methods for treating disorders caused by inappropriate cell proliferation, e.g. cancers, such as melanoma, lung cancers, pancreatic cancer, stomach, colon and rectal cancers, prostate and breast cancer, the leukemias and lymphomas, and the like. Anti-cancer compounds which can be converted to their nucleotide phosphonates for use as compounds of this invention include, but are not limited to, cytarabine (ara-C), fluorouridine, fluorodeoxyuridine (floxuridine), gemcitibine, cladribine, fludarabine, pentostatin (2'-deoxycoformycin), 6-mercaptopurine and 6-thioguanine and substituted or unsubstituted ara-adenosine (ara-A), ara-guanosine (ara-G), and ara-uridine (ara-U). Anticancer compounds of the invention may be used alone or in combination with other antimetabobtes or with other classes of anticancer drugs such as alkaloids, topoisomerase inhibitors, alkylating agents, antifumor antibiotics, and the like.

The prodrugs of the invention can be administered orally, parenterally, topically, rectally, and through other routes, with appropriate dosage units, as desired.

As used herein, the term "parenteral" refers to subcutaneous, intravenous, intra-arterial, intramuscular or intravitreal injection, or infusion techniques.

The term "topically" encompasses administration rectally and by inhalation spray, as well as the more common routes of the skin and mucous membranes of the mouth and nose and in toothpaste.

The term "effective amount" as applied to the phosphonate prodrugs of the invention is an amount that will prevent or reverse the disorders noted above. Particularly with respect to disorders associated with bone metabolism, an effective amount is an amount that will prevent, attenuate, or reverse abnormal or excessive bone resorption or the bone resorption that occurs in the aged, particularly post-menopausal females or prevent or oppose bone metastasis and visceral metastasis in breast cancer.

With respect to disorders associated with viral infections or inappropriate cell proliferation, e.g., cancer, the "effective amount" is determined with reference to the recommended dosages of the antiviral or anticancer parent compound. The selected dosage will vary depending on the activity of the selected compound, the route of administration, the severity of the condition being treated, and the condition and prior medical history of the patient being treated. However, it is within the skill of the art to start doses of the compound(s) at levels lower than required to achieve the desired therapeutic effect and to gradually increase the dosage until the desired effect is achieved. If desired, the effective daily dose may be divided into multiple doses for purposes of administration, for example, two to four doses per day. It will be understood, however, that the specific dose level for any particular patient will depend on a variety of factors, including the body weight, general health, diet, time, and route of administration and combination with other drugs, and the severity of the disease being treated.

Generally, the compounds of the present invention are dispensed in unit dosage form comprising 1% to 100% of active ingredient. The range of therapeutic dosage is from about 0.01 to about 1,000 mg/kg/day with from about 0.10 mg/kg/day to 100 mg/kg/day being preferred, when administered to patients, e.g., humans, as a drug. Actual dosage levels of active ingredients in the pharmaceutical compositions of this invention may be varied so as to administer an amount of the active compound(s) that is effective to achieve the desired therapeutic response for a particular patient.

A number of animal experiments have shown the efficacy of bisphosphonates in preventing bone loss under experimental conditions designed to mimic relevant clinical disorders. Based on these studies, several small animal model systems are available for evaluating the effects of bisphosphonates. These tests are also useful for measuring the comparative efficacy of the bisphosphonate prodrugs of the invention. The evaluation of bisphosphonate therapy typically requires the determination of femoral ash weight and bone mass, measured, for example as trabecular bone volume, between groups of treated and untreated animals. Thompson, D. et al. (1990) J. Bone and Mineral Res. 5(3):279-286, discloses use of such methods for evaluating the inhibition of bone loss in immobilized rats that were treated with aminohydroxybutane bisphosphonate. Yamamoto, M. et al. (1993) Calcif Tissue Int 53:278-282 induced hyperthyroidism in rats to produce bone changes similar to those in hyperthyroid humans, and compared bisphosphonate-treated and untreated groups biochemically, based on osteocalcin measurement, and by histomorphometric analysis, including differences in cancellous bone volume, and histological comparison of osteoid, osteoclast and osteoblast surfaces in bone sections. Seedor, J. G. et al. (1991) J. Bone and Mineral Res. 6(4):339-346 describes studies of the effect of alendronate in opposing bone loss in overactomized rats by femoral ash weight and histomorphometric analysis of tibial trabecular volume. The Schenk assay, comprising histological examination of the epiphyses of growing rats, can also be used as a screening assay. An exemplary screening test for evaluating the bone resorption opposing effects of the compounds of the invention in laboratory rats made osteopenic by various strategies is provided in Example 14.

Compounds of the invention can be prepared in a variety of ways, as generally depicted in Schemes I-VI. The general phosphonate esterification methods described below are provided for illustrative purposes only and are not to be construed as limiting this invention in any manner. Indeed, several methods have been developed for direct condensation of phosphonic acids with alcohols (see, for example, R. C. Larock, *Comprehensive Organic Transformations*, VCH, New York, 1989, p. 966 and references cited therein). Isolation and purification of the compounds and intermediates described in the examples can be effected, if desired, by any suitable separation or purification procedure such as, for example, filtration, extraction, crystallization, flash column chromatography, thin-layer chromatography, distillation or a combination of these procedures. Specific illustrations of suitable separation and isolation procedures are in the examples below. Other equivalent separation and isolation procedures can of course, also be used.

Scheme I outlines a synthesis of bisphosphonate prodrugs that contain a primary amino group, such as pamidronate or alendronate. Example 1 provides conditions for a synthesis of 1-O-hexadecyloxypropyl-alendronate (HDP-alendronate) or 1-O-hexadecyloxypropyl-pamidronate (HDP-pamidronate). In this process, a mixture oT dimethyl 4-phthalimidobutanoyl phosphonate (1b, prepared as described in U.S. Pat. No. 5,039,819)) and hexadecyloxypropyl methyl phosphite (2) in pyridine solution is treated with triethylamine to yield bisphosphonate tetraester 3b which is purified by silica gel chromatography. Intermediate 2 is obtained by transesterification of diphenyl phosphite as described in Kers, A., Kers, I., Stawinski, J., Sobkowski, M., Kraszewski, A. Synthesis, April 1995, 427-430. Thus, diphenyl phosphite in pyridine solution is first treated with hexadecyloxypropan-1-ol, then with methanol to provide compound 2.

Scheme I

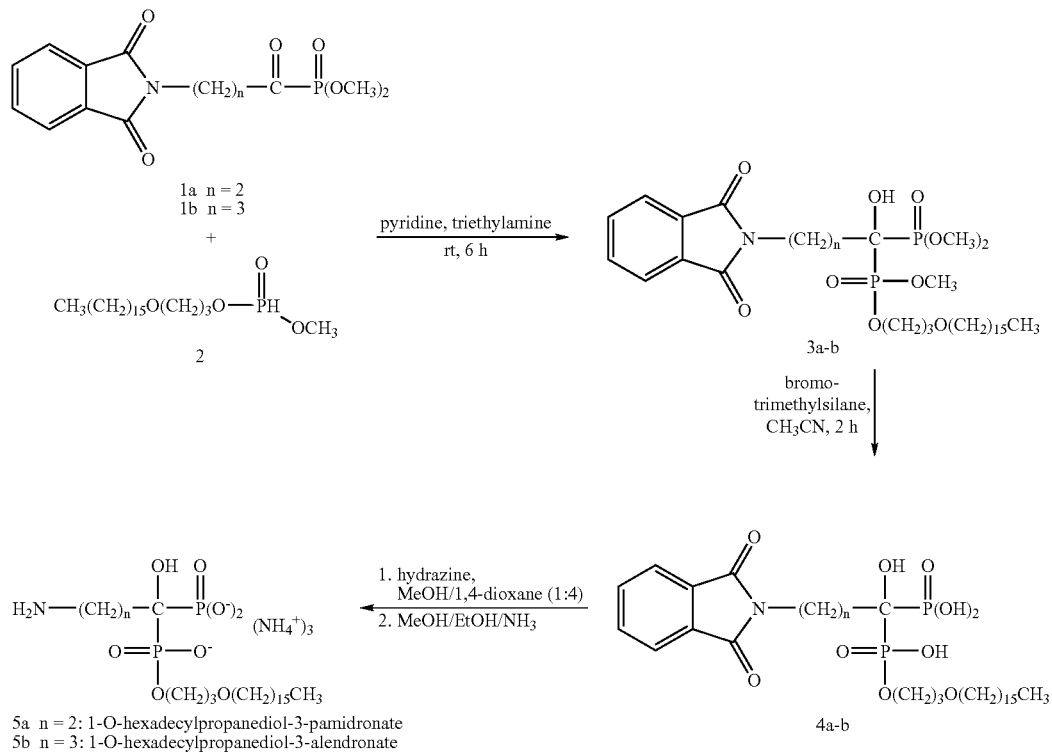

An important aspect of the process is that other long chain alcohols may be used in place of hexadecyloxypropan-1-ol to generate the various compounds of this invention. Treatment of intermediate 3b with bromotrimethylsilane in acetonitrile cleaves the methyl esters selectively to yield monoester 4b. Treatment of 4b with hydrazine in a mixed solvent system (20% melhanol/80% 1,4-dioxane) results in removal of the phthalimido protecting group as shown. The desired alendronate prodrug is collected by filtration and converted to the triammonium salt by treatment with methanolic ammonia.

Scheme II illustrates a synthesis of analogs of bisphosphonates lacking a primary amino group, hi this case the process steps are similar to those of Scheme 1 except that protection with a phthalimido group and subsequent deprotection by hydrazinolysis are unnecessary.

Scheme II

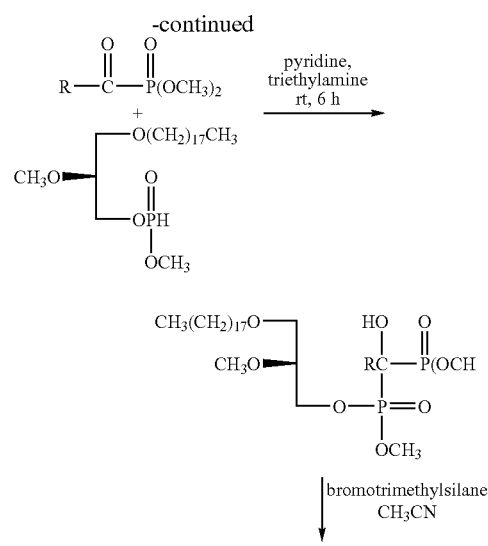

Bisphosphonates having 1-amino groups, such as amino-olpadronate, maybe converted to analogs according to the invention prodrugs using a slightly modified process shown in Scheme III.

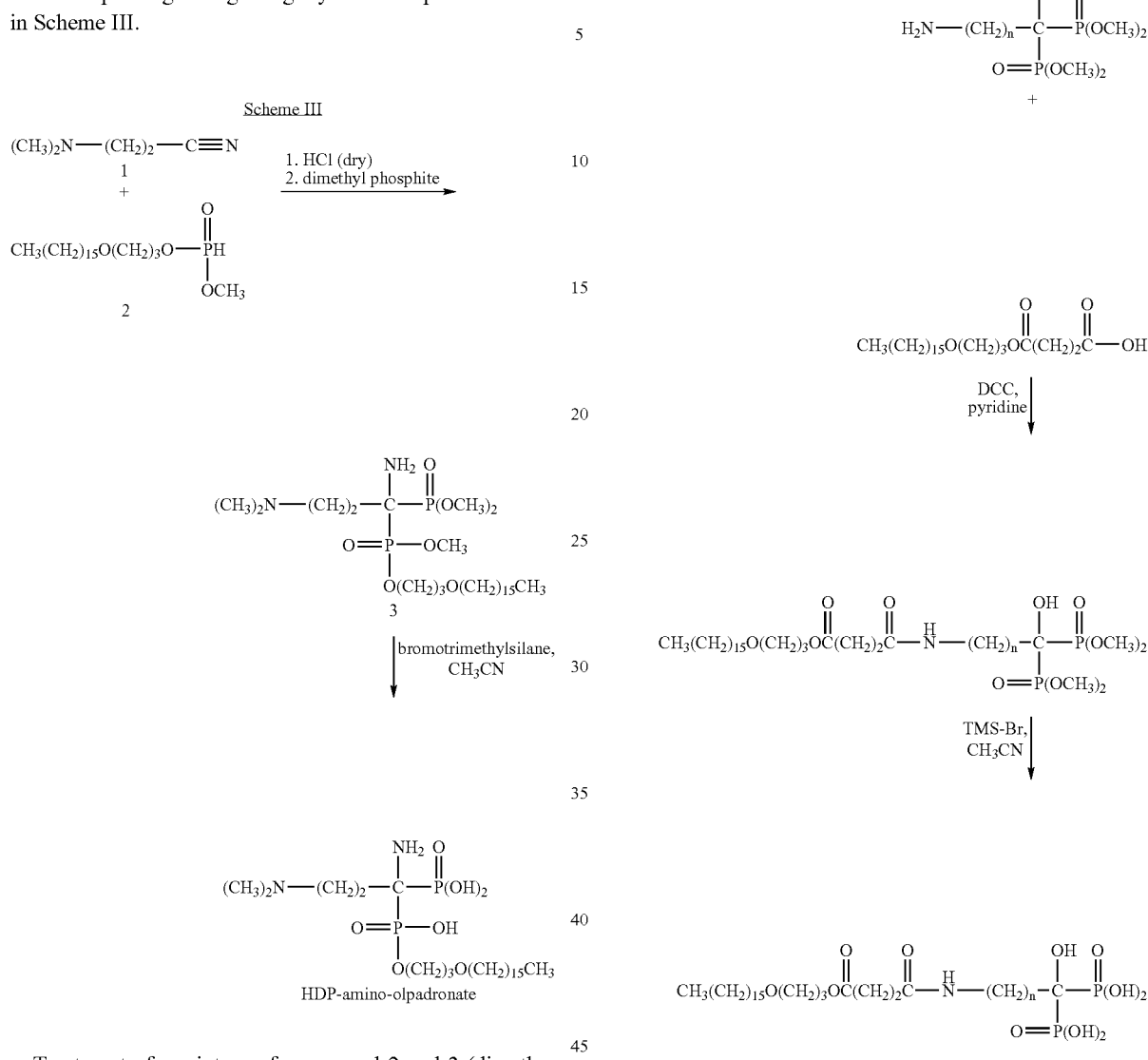

Treatment of a mixture of compound 2 and 3-(dimethylamino)propionitrile with dry HCl followed by addition of dimethyl phosphite affords tetraester 3 which, after demethylation with bromotrimethylsilane, yields hexadecyloxypropyl-amino-olpadronate.

Scheme IV illustrates synthesis of a bisphosphonate analog where the lipid group is attached to a primary amino group of the parent compound rather than as a phosphonate ester.

Scheme IV

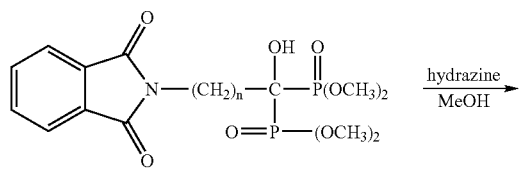

Scheme V illustrates a general synthesis of alkylglycerol or alkylpropanediol analogs of cidofovir, cyclic cidofovir, and other phosphonates. Treatment of 2,3-isopropylidene glycerol, 1, with NaH in dimethylformamide followed by reaction with an alkyl methanesulfonate yields the alkyl ether, 2. Removal of the isopropylidene group by treatment with acetic acid followed by reaction with trityl chloride in pyridine yields the intermediate 3. Alkylation of intermediate 3 with an alkyl halide results in compound 4. Removal of the trityl group with 80% aqueous acetic acid affords the O,O-dialkyl glycerol, 5. Bromination of compound 5 followed by reaction with the sodium salt of cyclic cidofovir or other phosphonate-containing nucleotide yields the desired phosphonate adduct, 7. Ring-opening of the cyclic adduct is accomplished by reaction with aqueous sodium hydroxide. The preferred propanediol species may be synthesized by substituting 1-O-alkylpropane-3-ol for compound 5 in Scheme V. The tenofovir and adefovir analogs may be synthesized by substituting these nucleotide phosphonates for cCDV in reaction (f) of Scheme V. Similarly, other nucleotide phosphonates of the invention may be formed in this manner.

Scheme V

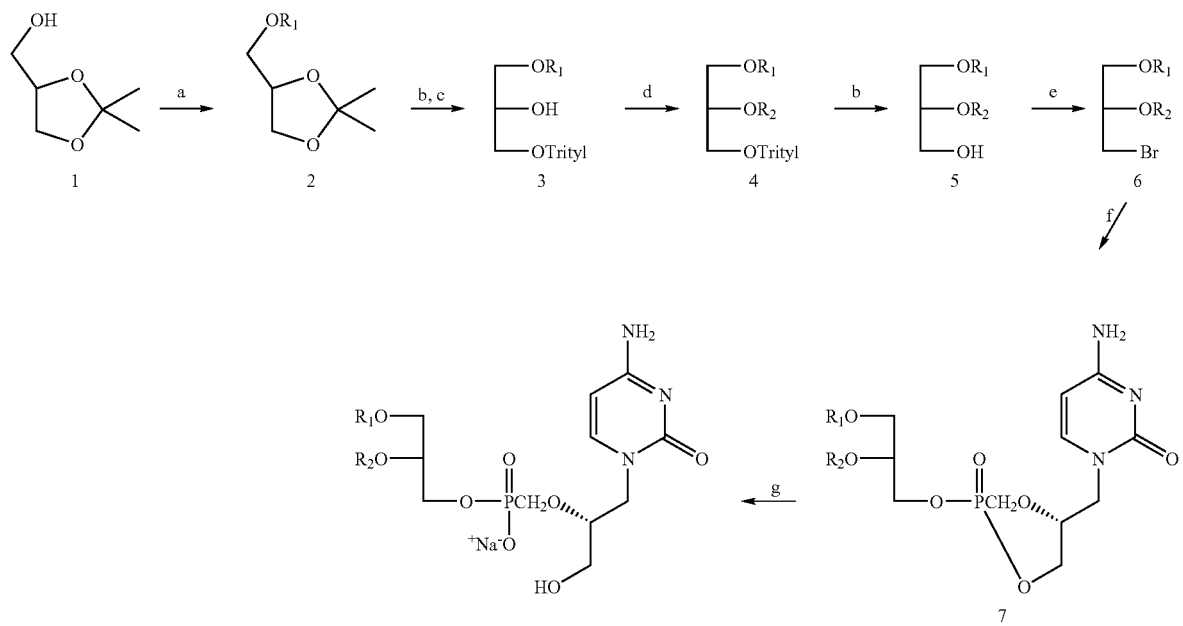

Reagents:
a) NaH, R₁OSO₂Me, DMF;
b) 80% aq acetic acid;
c) Trityl chloride, pyridine;
d) NaH, R₂—Br, DMF;
e) CBr₄, triphenylphosphine, THF;
f) cyclic cidofovir, (DCMC salt), DMF;
g) 0.5 N NaOH Scheme VI illustrates a general method for the sythesis of nucleotide phosphonates of the invention using 1-O-hexadecyloxypropyl-adefovir as the example. The nucleotide phosphonate (5 mmol) is suspended in dry pyridine and an alkoxyalkanol or alkylglycerol derivative (6 mmol) and 1,3-dicyclohexylcarbodiimde (DCC, 10 mmol) are added. The mixture is heated to reflux and stirred vigorously until the condensation reaction is complete as monitored by thin-layer chromatography. The mixture is then cooled and filtered. The filtrate is concentrated under reduced pressure and the residue s adsorbed on silica gel and purified by flash column chromatography (elution with approx. 9:1dichloromethane/methanol) to yield the corresponding phosphonate monoester.

Scheme VI

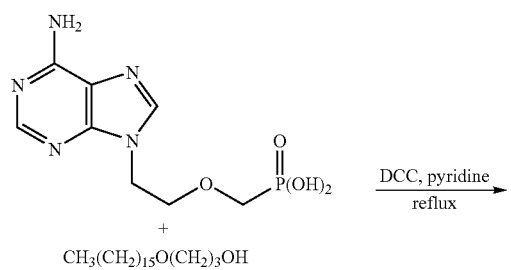

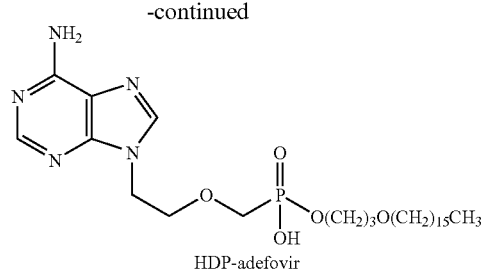

HDP-adefovir

The invention will now be described in greater detail by reference to the following non-limiting examples.

EXAMPLE 1

Synthesis of
1-O-hexadecylpropanediol-3-alendronate

A. HexadecyloxypropIyl methyl phosphite (b)

Hexadecyloxypropyl methyl phosphite was prepared using the method described in: Kers, A., Kers, I., Stawinski, J., Sobkowski, M., Kraszewski, A. Synthesis April 1995, 427-430. To a solution of diphenylphosphite (14 g, 60 mmol) in pyridine (50 mL) maintained at 0° C. was slowly added to a solution of hexadecyloxypropan-1-ol (6.0 g, 20 mmol) in pyridine (25 mL). The mixture was stirred one hour before anhydrous methanol (10 mL) was added. After stirring an additional hour, the solvent was evaporated the residue was adsorbed on silica gel and chromatographed, using gradient elution (hexanes to 20% ethyl acetate/80% hexanes), to afford pure compound 2 as a waxy, low-melting solid (4.5 g, 60% yield). $^1$H NMR (CDCl$_3$) δ 6.79 (d, 1H, J=696 Hz), 4.19 (q, 2H), 3.78 (d, 3H), 3.51 (t, 3H), 3.40 (t, 2H), 1.95 (pent, 2H), 1.25 (broad s, 28H), 0.88 (t, 3H).

B. Hexadecyloxypropyl trimethyl 4-phthalimidobutanoyl phosphonate (3b)

To a mixture of dimethyl 4-phthalimidobutanoyl phosphonate (1b, 3.0 g, 7.9 mmol, prepared as described in U.S. Pat. No. 5,039,819) and hexadecyloxypropyl methyl phosphite (2, 2.9 g, 9 mmol) in pyridine (50 mL) was added triethylamine (0.2 g, 2 mmol). The mixture was stirred 5 hours at room temperature, then the solvent was removed in vacuo. The residue was adsorbed on silica gel and chromatographed (ethyl acetate) to give compound 3b (3.5 g, 63%) as a viscous oil. $^1$H NMR (CDCl$_3$) δ 7.84 (d, 2H), 7.72 (d, 2H), 4.45 (m, 1H), 4.27 (m, 4H), 4.15 (q, 2H), 3.68 (s, 3H), 3.84 (s, 3H), 3.71 (t, 2H), 3.51 (m, 2H), 3.38 (t, 2H), 2.04 (m, 2H), 1.94 (pent., 2H), 1.54 (m, 2H), 1.25 (broad s, 28H), 0.88 (t, 3H). $^{31}$P NMR (22.54 (doublet), 21.22 (quartet)).

C. Hexadecyloxypropyl 4-phthalimidobutanoyl phosphonate (4b)

Compound 3b from above (3.0 g, 4.3 mmol) was dissolved in dry acetonitrile (50 mL) and cooled to 0° C. A solution of bromotrimethylsilane (3.9 g, 25.5 mmol) in acetonitrile (25 mL) was added slowly then the solution was stirred an additional 2 hours. The mixture was then poured slowly into crushed ice. The precipitate that formed was collected by vacuum filtration and dried in vacuo to give 1.2 g of 4b (42% yield). $^1$H NMR (DMSO-d$_6$) 7.86 (m, 4H), 3.99 (q, 2H), 3.66-3.55 (m, 1H), 3.54 (m, 2H), 3.35 (t, 2H), 3.27 (t, 2H), 1.89-1.80 (m,), 1.72 (pent., 2H), 1.53-1.40 (m,2H), 1.22 (broad s, 28H), 0.85 (t, 3H). 3IP NMR (21.51 (doublet), 19.50 (doublet)).

D. 1-O-Hexadececylpropanediol-3-alendronate (5b)

Compound 4b (300 mg, 0.45 mmol) was dissolved in a mixture of 1,4-dioxane (20 mL) and methanol (5 mL). Anhydrous hydrazine was then added and the mixture was stirred at room temperature for 4 hours. The precipitate that separated was collected by vacuum filtration and rinsed with 1,4-dioxane. The solid was then suspended in ethanol and methanolic ammonia (3 mL) was added. After stirring for 10 minute's the resulting solid was collected by filtration, rinsed with ethanol and dried under vacuum to yield 220 mg HDP-alendronate (5b) as the triammonium salt. Analysis by FT-IR indicated removal of the phthalimido protecting group. Electrospray MS m/e 532 (MH+), 530 (MH).

EXAMPLE 2

Synthesis of 1-O-bexadecylpropanediol-3-pamidronate (5a)

1-O-hexadecylpropanediol-3-pamidronate is prepared in an analogous manner (according to Scheme 1) except that 3-phthalimidopropanoic acid is used to prepare dimethyl 3-phthalimidopropanoyl phosphonate (1a). Compound 1a is condensed with 2 to yield the trimethyl bisphosphonate 3a. Deprotection as in Steps C and D above yields HDP-pamidronate as shown.

EXAMPLE 3

Synthesis of 1-O-Octadecyl-2-O-methyl sn-glycero-3-alendronate

Prodrugs with lipophilic groups other than hexadeclyoxypropyl are prepared by substituting various long-chain alcohols for hexadecyloxypropan-1-ol in Step A of Example 1. For example, reaction of 1-O-Octadecyl-2-O-methyl-sn-glycerol with diphenylphosphite in pyridine followed by treatment with methanol gives 1-O-octadecyl-2-O-methyl-sn-glyceryl methyl phosphite. Condensation of this dialkylphosphite with phosphonate 1b, followed by deprotection steps C and D gives 1-O-Octadecyl-2-O-methyl-sn-glycero-3-alendronate. Scheme 2 illustrates a synthesis of other bisphosphonate conjugates which do not have a primary amino group in the side chain. In this case protection with a phthalimido group and deprotection by hydrazinolysis are unnecessary.

EXAMPLE 4

Synthesis of HDP-amino-olpadronate

Scheme 3 illustrates the synthesis of 1-amino bisphosphonate conjugates. Using compound 2 from Example 1, 3-(dimethylamino)propionitrile, and procedures described in: Orlovskii, V. V.; Vovsi, B. A. J. Gen Chem. USSR (Engl. Transl.) 1976, 46: 294-296, the bisphosphonate trimethyl ester 3 is prepared. Demethylation with bromotrimethylsilane as described in step C of Example 1 provides HDP-amino-olpadronate.

EXAMPLE 5

Synthesis of 1-O-Hexadecylpropanediol-3-succinyl-alendronate

Scheme 4 illustrates the synthesis of a bisphosphonate conjugate wherein the lipid group is attached to a primary amino group of the parent compound. Tetramethyl-(4-phthalimido-1-hydroburylidene)bisphosphonate (2.0 g, 4.4 mmol) was dissolved in 0.2M methanolic hydrazine (100 mL), and the solution stirred at room temperature for 3 days. The mixture was concentrated to half its volume when a solid started separating. The solid was filtered off and the filtrate concentrated to dryness. Proton NMR showed this compound to be tetramethyl-(4-amino-1-hydroxybutylidene)bisphosphonate. This was dried over phosphorus pentoxide at 50° C. overnight. To a suspension of 1.2 g of the compound in a mixture of pyridine (25 mL) and N,N-dimethylformamide (25 mL) was added 3-succinyl-1-hexdeclyoxypropane (1.76 g, 4.4 mmol). Dicyclohexyl carbodiimide (2.52 g, 12.21 mmol) was added and the mixture stirred at room temperature for two days. The mixture was filtered; the filtrate was absorbed on silica gel and flash chromatographed with an increasing gradient of methanol in dichloromethane (0%-20%) to yield succinylated compound. This was deblocked with trimethylsilyl bromide in acetonitrile to yield the title compound which was purified by crystallization from methanol.

EXAMPLE 6

Synthesis of Adefovir Hexadecyloxypropyl and 1-O-Octadecyl-sn-glyceryl Esters To a mixture of adefovir (1.36 g, 5 mmol) and 3-hexadecyloxy-1-propanol (1.8 g, 6 mmol) in dry pyridine was added DCC (2.06 g, 10 mmol). The mixture was heated to reflux and stirred 18 h then cooled and filtered. The filtrate was concentrated under reduced pressure and the residue was applied to a short column of silica gel. Elution of the column with 9:1 dichloromethane/methanol yielded hexadecyloxypropyl-adefovir (HDP-ADV) as a white powder.

To a mixture of adefovir (1.36 g, 5 mmol) and 1-O-octadecyl-sn-glycerol (2.08 g, 6 mmol) in dry pyridine (30 mL) was added DCC (2.06 g, 10 mmol). The mixture was heated to reflux and stirred overnight then cooled and filtered. The filtrate was concentrated under reduced pressure and the residue was applied to a column of silica gel. Elution of the column with a 9:1 dichloromethane/methanol yielded 1-O-octadecyl-sn-glyceryl-3-adefovir.

EXAMPLE 7

Synthesis of AZT-phosphonate Hexadecyloxypropyl Ester

The phosphonate analog of AZT (3'-Azido-5'-S'-dideoxythymidine-S'-phosphonic acid) was synthesized using the published procedure: Hakimelahi, G. H.; Moosavi-Movahedi, A. A.; Sadeghi, M. M.; Tsay, S-C; Hwu, J. R. Journal of Medicinal Chemistry, 1995 38, 4648-4659.

The AZT phosphonate (1.65 g, 5 mmol) was suspended in dry pyridine (30 mL), then 3-hexadecyloxy-1-propanol (1.8 g, 6 mmol) and DCC (2.06 g, 10 mmol) were added and the mixture was heated to reflux and stirred for 6 h, then cooled and filtered. The filtrate was concentrated under reduced pressure and the residue was applied to a column of silica gel. Elution of the column with a 9:1 dichloromethane/methanol yielded 3'-azido-3'-5'-dideoxythymidine-5'-phosphonic acid, hexadecyloxypropyl ester.

EXAMPLE 8

Synthesis of the Hexadecyloxypropyl, Octadecyloxypropyl, Octadecyloxyethyl and Hexadecyl Esters of Cyclic Cidofovir To a stirred suspension of cidofovir (1.0 g, 3.17 mmol) in N,N-DMF (25 mL) was added N,N-dicyclohexyl-4-morpholine carboxamidine (DCMC, 1.0 g, 3.5 mmol). The mixture was stirred overnight to dissolve the cidofovir. This clear solution was then charged to an addition funnel and slowly added (30 min.) to a stirred, hot pyridine solution (25 mL, 60° C.) of 1,3-dicyclohexyl carbodiimide (1.64 g, 7.9 mmol). This reaction mixture was stirred at 100° C. for 16 h then cooled to room temperature, and the solvent was removed under reduced pressure. The residue was adsorbed on silica gel and purified by flash column chromatography using gradient elution ($CH_2Cl_2$+MeOH). The UV active product was finally eluted with 5:5:1 $CH_2Cl_2$/MeOH/$H_2O$ Evaporation of the solvent gave 860 mg of a white solid. The $^1H$ and $^{31}P$ NMR spectrum showed this to be the DCMC salt of cyclic cidofovir (yield=44%).

To a solution of cyclic cidofovir (DCMC salt) (0.5 g, 0.8 mmol) in dry DMF (35 mL) was added 1-bromo-3-hexadecyloxypropane (1.45 g, 4 mmol) and the mixture was stirred and heated at 80° C. for 6 h. The solution was then concentrated in vacuo and the residue adsorbed on silica gel and purified by flash column chromatography using gradient elution ($CH_2Cl_2$+EtOH). The alkylated product was eluted with 90:10 $CH_2Cl_2$/EtOH. The fractions containing pure product were evaporated to yield 260 mg HDP-cyclic cidofovir (55% yield).

To a solution of cyclic cidofovir (DCMC salt) (1.0 g, 3.7 mmol) in dry DMF (35 mL) was added 1-bromo-3-octadecyloxypropane (2.82 g, 7.2 mmol) and the mixture was stirred and heated at 85° C. for 5 h. The solution was then concentrated in vacuo and the residue adsorbed on silica gel and purified by flash column chromatography using gradient elution ($CH2Cl2$+MeOH). The alkylated product was eluted with 9:1 $CH_2Cl_2$/MeOH. The fractions containing pure product were evaporated to yield 450 mg ODP-cyclic cidofovir.

To a solution of cCDV (DCMC salt) (1.0 g, 3.7 mmol) in dry DMF (35 mL) was added 1-bromo-3-octadecyloxyethane (3.0 g, 7.9 mmol) and the mixture was stirred and heated at 80° C. for 4 h. The solution was then concentrated in vacuo and the residue adsorbed on silica gel and purified by flash column chromatography using gradient elution ($CH_2Cl_2$+MeOH). The alkylated product was eluted with 9:1 $CH_2Cl_2$/MeOH. The fractions containing pure product were evaporated to yield 320 mg octadecyloxyethyl-cCDV.

To a solution of cyclic cidofovir (DCMC salt) (0.5 g, 0.8 mmol) in dry DMF (35 mL) was added 1-bromo-hexadecane (1.2 g, 4 mmol) and the mixture was stirred and heated at 80° C. for 6 h. The solution was then concentrated in vacuo and the residue adsorbed on silica gel and purified by flash column chromatography using gradient elution ($CH_2Cl_2$+MeOH). The alkylated product was eluted with 9:1 $CH_2Cl_2$/MeOH. The fractions containing pure product were evaporated to yield 160 mg hexadecyl-cCDV.

EXAMPLE 9

Synthesis of the Hexadecyloxypropyl, Octadecyloxypropyl, Octadecyloxyethyl and Hexadecyl Esters of Cidofovir Hexadecyloxypropyl-cyclic CDV from above was dissolved in 0.5 M NaOH and stirred at room temp for 1.5 h. 50% aqueous acetic was then added dropwise to adjust the pH to about 9. The precipitated HDP-CDV was isolated by filtration, rinsed with water and dried, then recrystallized (3:1 p-dioxane/water) to give HDP-CDV.

Similarly, the octadecyloxypropyl-, octadecyloxyethyl- and hexadecyl-cCDV esters were hydrolyzed using 0.5 M NaOH and purified to give the corresponding cidofovir diesters.

EXAMPLE 10

Synthesis of cyclic-ganciclovir phosphonate Hexadecyloxypropyl Ester

The cyclic phosphonate analog of ganciclovir was prepared using the published procedure: (Reist, E. J.; Sturm, P. A.; Pong, R. Y.; Tanga, M. J. and Sidwell, R. W. Synthesis of acyclonucleoside phosphonates for evaluation as antiviral agents, p. 17-34. In J, C. Martin (ed.), Nucleotide Analogues as Antiviral Agents, American Chemical Society, Washington, D.C). After conversion to the DCMC salt in DMF the cGCV phosphonate was treated with 1-bromo-3-hexadecyloxypropane and the mixture was heated to 80° C. for 6 hours.

Isolation of the alkylated product by flash chromatography yielded HDP-cyclic-GCV phosphonate.

EXAMPLE 11

Synthesis of ganciclovir pbosphonate hexadecyloxypropyl ester

HDP-cyclic GCV phosphonate from above was dissolved in 0.5 M NaOH and stirred at room temperature to convert it to the acyclic diester. The solution was neutralized with 50% aq acetic acid to precpitate the product which was recrystallized in 3:1 p-dioxane/water.

EXAMPLE 12

1-O-Hexadecyloxypropane Alendronate Inhibits Dexametbasone-Induced Apoptosis of MLO-Y4 Osteocytic Cells MLO-Y4 osteocytic cells were pretreated with the indicated concentration of 1-O-hexadecyloxypropane alendronate (HDP-alendronate) for 1 hour, and subsequently the cells were incubated for 6 hours with and without dexamethasone ($10^{-4}$ M final concentration). The percentage of dead cells was determined by trypan blue update (Plotkin et al., J Clin Invest 104:1363-1374, 1999). Results are presented in FIG. 1. Bars represent the mean±SD of 3 independent measurements. Data were analyzed by 1-way ANOVA (Student-Keuls-Newman test). *p<0.05. HDP-alendronate inhibits dexamethasone-induced apoptosis at $10^{-8}$ to $10^{-5}$ M.

EXAMPLE 13

Figure 2:
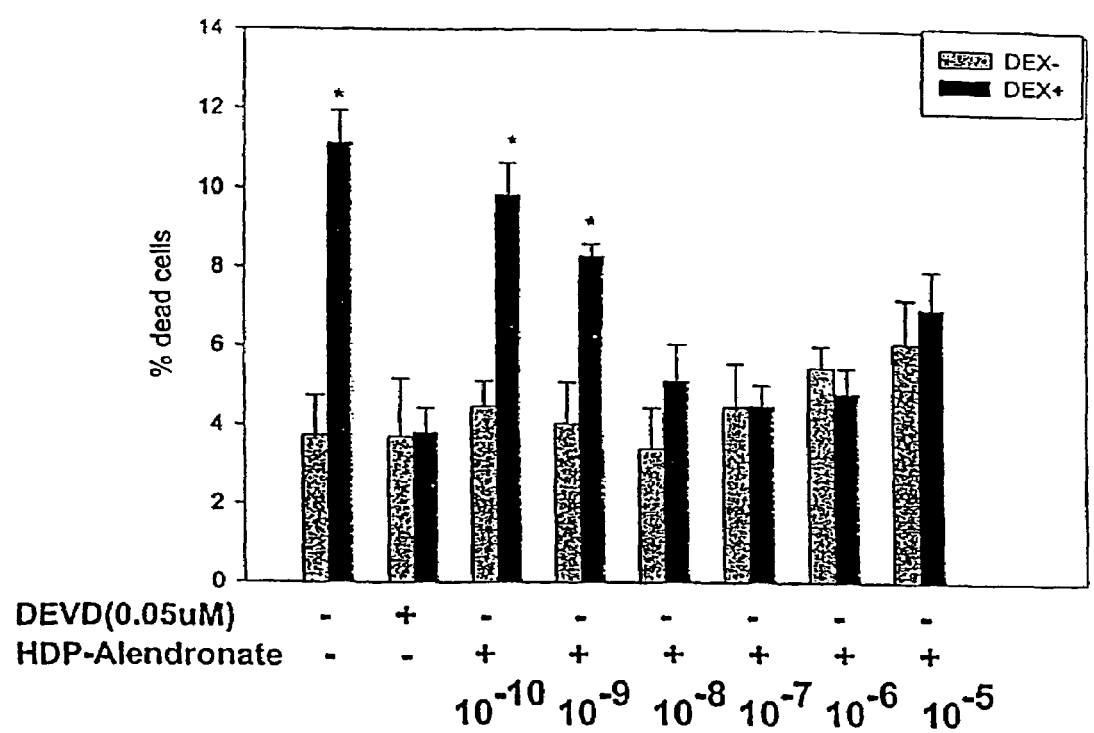
FIG. 2 summarizes the effect of a compound according to the invention, 1-O-hexadecyloxypropane alendronate, on dexamethasone-induced apoptosis of calvarial cells. Bars represent the mean±SD of 3 independent measurements. Gray bars represent the absence of dexamethasone and black bars represent the presence of $10^{-4}$ M dexamethasone.

1-O-Hexadecyloxypropane Alendronate Inhibits Dexamethasone-induced Apoptosis in Calvarial Cells Calvarial cells were obtained from neonatal C57BL/6J mice and passaged in tissue culture. The cells were pretreated with the indicated concentration of HDP-alendronate for 1 hour, and subsequently the cells were incubated for 6 hours with and without $10^{-4}$ dexamethasone. The percentage of dead cells was determined by trypan blue uptake (Plotkin, L. et al., J Clin Invest 104:1363-1374, 1999). Results are presented in FIG. 2. Bars represent the mean±SD of 3 independent measurements. Data were analyzed by 1-way ANOVA (Student-Keuls-Newman test). *p<0.05. Pretreatment of cells with HDP-alendronate at $10^{-8}$ or greater abolished the dexametEasone-induced increase in % dead cells (p=<0.05). Cells exposed to 0.05 μM DEVD (a peptide inhibitor of apoptosis) followed by dexamethasone did not exhibit an increase in % dead cells demonstrating that DEVD blocks dexamethasone-induced apoptosis.

EXAMPLE 14

Inhibition of Bone Resorption in Ovariectomized Rats by 1-O-hexadecylpropane alendronate Members of groups of (250 gm-280 gm) female Sprague-Dawley rats that have undergone bilateral ovariectomy are treated either with 4-amino-1-hydroxybutylidene-1,1-bis-phosphonic acid, disodium salt or 1-O-hexadecylpropanediol-3-alendronate injected subcutaneously in graduated doses of from 0 mg/kg/day to 8 mg/kg/day, for a period of four to twelve weeks. At twelve weeks the rats, including members of a control group, are sacrificed and the femora of each animal is ashed. Alternatively, the method of administration may be oral. The ash weight of the femora for each individual is determined, the values for each group compared as an indicator of bone mass to determine relative inhibition of bone loss among the treatment protocols. 1-O-hexadecylpropane alendronate-treated animals exhibit less bone mass loss than the ovariectomized controls.

EXAMPLE 15

Inhibition of Bone Resorption in Humans with Osteoporosis by 1-O-octadecyloxypropyl-alendronate Two groups of postmenopausal women are treated with placebo or with 1-O-octadecyloxypropyl-alendronate at an oral dose of from 0.1 mg/kg/day to 100 mg/kg/day for a period of from two to three years. Members of the treatment groups are continually monitored over the course of treatment for bone mineral density, incidence of vertebral fractures, progression of vertebral deformities by radiographic examination and height loss. Comparisons of measurements are made among the various treatment groups to determine the effectiveness of the forms of alendronate therapy among the treatment group. The group treated with 1-O-octadecyloxypropyl alendronate will have fewer fractures and a lesser rate of reduction in bone density than the placebo group.

EXAMPLE 16

Stimulation of Bone Formation in Humans with Steroid-Induced Osteoporosis by 1-O-octadecyloxypropyl-amino-Olpadronate Groups of patients with steroid-induced osteoporosis are treated with 1-O-octadecyloxypropyl-amino-olpadronate or placebo at an oral dose of from 0.1 mg/kg/day to 100 mg/kg/day for a period of from one month to one year. Members of the treatment groups are continually monitored over the course of treatment for bone mineral density, incidence of vertebral fractures, progression of vertebral deformities by radiographic examination and height loss. Comparisons of measurements are made among the various treatment groups to determine the effectiveness of 1-O-octadecyloxypropyl-amino-olpadronate therapy among the treatment group. Compared with placebo treatment, bone density is increased and fractures are decreased in 1-O-octadecyloxypropyl-amino-olpadronate-treated patients.

EXAMPLE 17

Antiviral Activity and Selectivity of Phosphonate Nucleotide Analogs Against Human Cytomegalovirns (HCMV)

HCMV antiviral assay: Antiviral assays for HCMV DNA were carried out by DNA hybridization as reported by Dankner, W. M., Scholl, D., Stanat, S. C., Martin, M., Souke, R. L. and Spector, S. A., J. Virol. Methods 21:293-298, 1990. Briefly, subconfluent MRC-5 cells in 24-well culture dishes were pretreated for 24 h with various concentrations of drug in Eagle s minimum essential medium (E-MEM) containing 2% FBS and antibiotics. The medium was removed and HCMV strains added aba dilution that will result in a 3-4+ cytopathic effect (CPE) in the no-drug wells in 5 days. The virus was absorbed for 1' h at 37° C., aspirated and replaced with the drug dilutions. After 5 days of incubation HCMV DNA was quantified in triplicate by nucleic acid hybridization using a CMV Antiviral Susceptibility Test Kit from Diagnostic Hybrids, Inc. (Athens, Ohio). The medium was removed and cells lysed according to the manufacturer s instructions. After absorption of the lysate, the Hybriwix™ filters were hybridized overnight at 60° C. The Hybriwix™ were washed for 30 min at 73° C. and counted in a gamma counter. The results are expressed as $EC_{50}$ (the 50% inhibitory concentration).

Preliminary experiments were performed on 1-O-hexadecylpropanediol (HDP) derivatives of cidofovir and adefovir, as shown in Table 1.

TABLE 1

| Drug | HCMV $EC_{50}$, μM | CEM, $CC_{50}$, μM | Selectivity Index |
|---|---|---|---|
| CDV | 0.45 ± 0.09 (3) | 857 | 1,900 |
| cCDV | 0.47 ± 0.13 (3) | >1000 | >2,100 |
| HDP-cCDV | 0.0005 (2) | 30 | 59,600 |
| Adefovir | 55 (1) | | |
| HDP-Adefovir | 0.01 (1) | — | — |

As the results in Table 1 indicate, 1-O-hexadecylpTopanediol-3-cyclic CDV (HDP-cCDV) was >900 times more active than CDV or cyclic CDV. While more cytotoxic, the selectivity index against HCMV in rapidly dividing cells was >59,000 vs. 1,900 to >2,100 for the underivatized CDV's. Based on these promising preliminary results, further experiments were carried out using additional invention compounds. These further experiments are described as follows.

Cytotoxicity of test compounds in vitro: Subconfluent human lung fibroblast cells (MRC-5, American Type Culture Collection, Rockville, Md.) in 24-well plates were treated with drugs diluted in E-MEM (Gibco BRL, Grand Island, N.Y.) supplemented with 2% fetal bovine serum and antibiotics. After 5 days of incubation at 37° C., the cell monolayer was visually inspected under magnification and the concentration of drug which caused a 50% reduction in cell number was estimated.

The data obtained from these experiments is shown in Table 2.

TABLE 2

Inhibition of Human CMV Replication in MRC-5 Human Lung Fibroblasts Assayed by DNA Reduction

| Compound | $EC_{50}$, μM | $CC_{50}$, μM | Selectivity Index |
|---|---|---|---|
| Cidofovir (CDV) | 0.46 | >1000 | >2174 |
| Cyclic Cidofovir (cDCV) | 0.47 | >1000 | >2128 |
| 1-O-hexadecylpropanediol-3-CDV | $2 \times 10^{-6}$ | 10 | $5 \times 10^6$ |
| 1-O-hexadecylpropanediol-3-cCDV | $3 \times 10^{-4}$ | 320 | $1 \times 10^6$ |
| 1-O-octadecylpropanediol-3-CDV | $3 \times 10^{-5}$ | 32 | $1 \times 10^6$ |
| 1-O-octadecylpropanediol-3-cCDV | $3 \times 10^{-4}$ | 320 | $1 \times 10^6$ |
| 1-O-octadecylethanediol-2-CDV | $>1 \times 10^{-9}$ | 210 | $2 \times 10^{11}$ |
| 1-O-octadecylethanediol-2-cCDV | $3 \times 10^{-4}$ | 320 | $1 \times 10^6$ |
| Hexadecyl-cCDV | 0.04 | 6.5 | 163 |
| Adefovir (ADV) | 55 | >1000 | >18 |
| 1-O-hexadecylpropanediol-3-ADV | 0.10 | 6.5 | 65 |
| 1-O-octadecyl-sn-glycero-3-ADV | 0.21 | — | — |

$EC_{50}$—50% effective concentration;
$CC_{50}$—50% cytotoxic concentration;
selectivity index—$CC_{50}/EC_{50}$.
$EC_{50}$ results are the average of 3 to 6 determinations, with the exception that ADV is a single replication done in duplicate As the results shown in Table 2 indicate, compounds of the invention are uniformly more active and selective than underivatized cidofovir, cyclic cidofovir and adefovir.

EXAMPLE 18

Effect of HDP-cCDV on Poxvirus Replication, In Vitro

The activity of cidofovir (CDV), cyclic cidofovir (cCDV), and 1-O-hexadecylpropanediol-3-cCDV (HDP-cCDV) were tested for antiviral activity in human foreskin fibroblasts infected with vaccinia virus or cowpox virus by measuring the dose dependent reduction in cytopathic effect (CPE). Preliminary vaccinia and cowpox $EC_{50}$ values were determined in a CPE reduction assay in human foreskin fibroblast (HFF) cells. The data thus obtained is shown in Table 3.

TABLE 3

| Drug | Vaccinia $EC_{50}$, μM | Cowpox, EC50, μM | HFF Cells, CC50, μM |
|---|---|---|---|
| CDV | 1.80 | 2.10 | 89.8 |
| Cyclic CDV | 0.97 | 0.72 | >100 |
| HDP-cCDV | 0.11 | <0.03 | >100 |
| Control lipid | >100 | >100 | >100 |

As shown in Table 3, HDP-cCDV was highly active against vaccinia virus with an $1C_{50}$ value of 0.11 μM versus 0.97 and 1.8 μM for cCDV and CDV, respectively. In cowpox infected cells HDP-cCDV was extremely effective with an $IC_{50}$ of <0.03 μM versus 0.72 and 2.1 for cCDV and CDV, respectively. Based on this promising preliminary data, the effects of invention cidofovir analogs on the replication of other orthopox viruses was investigated.

Poxvirus Antiviral Cytopathic Effect (CPE) Assay: At each drug concentration, three wells containing Vero cells were infected with 1000 pfu/well of orthopoxyinis and three others remained uninfected for toxicity determination. Plates were examined and stained after the virus-infected, untreated cells showed 4+CPE. Neutral red was added to the medium and CPE was assessed by neutral red uptake at 540 ran. The 50% inhibitory (EC50) and cytotoxic concentrations (CC50) were determined from plots of the dose response. The results are shown in Table 4.

TABLE 4

| Compound | Vaccinia | Cowpox | EC50, µM Variola Major, Bangladesh | Variola Major, Yamada | Variola Minor, Garcia | $CC_{50}$ µM |
|---|---|---|---|---|---|---|
| CDV | 2.2 | 3.8 | 100 | — | — | >100 |
| cCDV | — | — | 100 | — | — | >100 |
| HDP-CDV | <0.03 | <0.03 | 0.0015 | 0.0015 | 0.0006 | >0.1 |
| HDP-cCDV | 0.11 | <0.03 | >

TABLE 7-continued

Inhibition of Human HSV Replication in MRC-5 Human Lung Fibroblasts Assayed by DNA Reduction

| Compound | $EC_{50}$, μM | $CC_{50}$, μM | Selectivity Index |
| --- | --- | --- | --- |
| 1-O-hexadecylpropanediol-3-CDV | $4 \times 10^{-7}$ | 10 | $25\ 10^6$ |
| 1-O-hexadecylpropanediol-3-cCDV | 0.030 | 320 | 10,667 |
| 1-O-octadecylpropanediol-3-CDV | 0.003 | 32 | 10,667 |
| 1-O-octadecylpropanediol-3-cCDV | 0.330 | 320 | 970 |
| 1-O-octadecylpropanediol-2-CDV | 0.002 | 210 | 105,000 |
| 1-O-octadecylpropanediol-2-cCDV | 0.008 | 320 | 40,000 |

Abbreviations as in Table 2.
$EC_{50}$—50% effective concentration;
$CC_{50}$—50% cytotoxic concentration;
selectivity index—$CC_{50}/EC_{50}$.
$EC_{50}$ values are the average of two experiments with the exception of HDP-CDV which is a single determination in duplicate.

As shown in Table 7, all invention compounds are more active against HSV-1 than the underivatized nucleotide phosphonates, cidofovir or cyclic cidofovir.

Although the foregoing invention has been described in some detail by way of illustration and example for purposes of clarity and understanding, it will be apparent to those of ordinary skill in the art in light of the teaching of this invention that certain changes and modifications may be made thereto without departing from the spirit or scope of the claims.

What is claimed is:

1. A method for the treatment of a viral disease selected from human immunodeficiency virus, influenza, herpes simplex virus, human herpes virus, cytomegalovirus, hepatitis B and C virus, Epstein-Barr virus, varicella zoster virus, orthopox virus, ebola virus and papilloma virus comprising administering an effective amount of a compound optionally in a pharmaceutically acceptable carrier, wherein said compound is a compound having the structure (A):

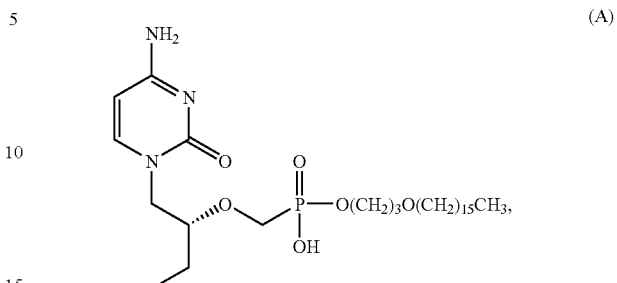

or a pharmaceutically acceptable salt thereof.

2. The method of claim 1, wherein the virus is an orthopox virus selected from variola major and minor, vaccinia, smallpox, cowpox, camelpox and monkeypox.

3. The method of claim 1, wherein the virus is human immunodeficiency virus.

4. The method of claim 1, wherein the virus is influenza.

5. The method of claim 1, wherein the virus is herpes.

6. The method of claim 1, wherein the virus is cytomegalovirus.

7. The method of claim 1, wherein the virus is hepatitis B.

8. The method of claim 1, wherein the virus is hepatitis C.

9. The method of claim 1, wherein the virus is Epstein-Barr virus.

10. The method of claim 1, wherein the virus is varicella zoster virus.

11. The method of claim 1, wherein the virus is papilloma.

* * * * *